(12) United States Patent
Elias

(10) Patent No.: US 6,365,138 B1
(45) Date of Patent: Apr. 2, 2002

(54) COMPOSITIONS FOR METABOLIC PROTECTION AND REPAIR OF LIPS

(75) Inventor: Peter M. Elias, Mill Valley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/545,130

(22) Filed: Apr. 7, 2000

(51) Int. Cl.⁷ .............................. A61K 7/00; A61K 7/04
(52) U.S. Cl. ........................ 424/64; 424/401; 514/558; 514/579
(58) Field of Search ................................ 424/401, 420, 424/424, 450, 64

(56) References Cited

U.S. PATENT DOCUMENTS

| 5,643,899 | A | * | 7/1997 | Elias et al. |
| 5,662,929 | A | * | 9/1997 | Lagace et al. |
| 5,723,114 | A | | 3/1998 | Thomfeldt et al. |
| 6,054,433 | A | | 4/2000 | Elias et al. |

* cited by examiner

*Primary Examiner*—Diana Dudash
*Assistant Examiner*—Gina C Yu
(74) *Attorney, Agent, or Firm*—Townsend and Townsend and Crew LLP

(57) ABSTRACT

An effective barrier function for the lips is restored and maintained by the topical administration of various formulations, including mixtures of ceramides and essential and nonessential free fatty acids, and mixtures of a β-glucocerebrosidase and a phospholipase $A_2$.

9 Claims, No Drawings

COMPOSITIONS FOR METABOLIC PROTECTION AND REPAIR OF LIPS

STATEMENT AS TO RIGHTS TO INVENTIONS MADE UNDER FEDERALLY SPONSORED RESEARCH AND DEVELOPMENT

This invention was made with government support by the Veterans Administration. The government has certain rights in this invention.

BACKGROUND OF THE INVENTION

1. Field of the Invention

This invention resides in the field of topical compositions for use in treating lips suffering from cracking, fissuring, or scaling as a result of xeric stress, and for preventing the occurrence of such conditions.

2. Description of the Prior Art

The lips are a mucosal epithelium, unique among other mucosal tissues because the constant exposure of the lips to the environment requires the lips to function as epidermal tissue. Lips demonstrate a less efficient barrier function than other epidermal tissues, however, and are therefore more susceptible to moisture loss and the detrimental effects that result from xeric stress.

SUMMARY OF THE INVENTION

This invention arises from the discovery that a reason for the inability of the lips to provide an efficient barrier function is that they are low in certain lipid processing enzymes that are needed to generate some of the lipids that contribute to an effective barrier function. In particular, the lips have relatively low levels of endogenous β-cerebrosidase and phospholipases, and accordingly the lips contain relatively large amounts of glucosylceramides and phospholipids that have not been converted by these enzymes to ceramides and free fatty acids. Since the resulting lipid mixture is low in its levels of these lipids, it is not an efficient composition for supporting the barrier function. This renders hence lips more susceptible to dehydration, which leads to cracking, fissuring and scaling.

In accordance with this invention, therefore, it has been discovered that xeric stress of the lips can be treated or prevented by the application of any of several topical formulations, as follows:

(1) Formulations in which the only lipids included in the formulations that are physiologically active in affecting the moisture content of the lips are:
  (a) one or more ceramides,
  (b) one or more essential free fatty acids, and
  (c) one or more nonessential free fatty acids; and
(2) Formulations that contain:
  (a) a β-glucocerebrosidase or an analog thereof that has substantially similar activity in converting glucosylceramides to ceramides, and/or
  (b) a phospholipase $A_2$ or an analog thereof that has substantially the same activity in converting phospholipids to free fatty acids.

DETAILED DESCRIPTION OF THE INVENTION AND SPECIFIC EMBODIMENTS

The term "ceramides" refers to a class of compounds that are otherwise known as "sphingoid" compounds or "sphingolipids." These compounds have a backbone of sphingosine or a closely related structure, with fatty acids linked to the backbone through an amide linkage at the amino group of the sphingosine structure. The generic formula for ceramides is as follows:

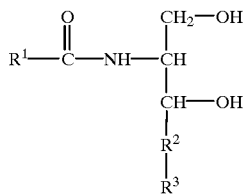

in which:
$R^1$ is alkyl or α-hydroxyalkyl;
$R^2$ is either

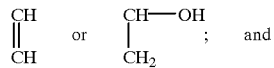

$R^3$ is $C_{10}$–$C_{20}$ alkyl.

The term "alkyl" as it is used herein includes both straight-chain and branched-chain groups, saturated and unsaturated (i.e., containing one or more double bonds), and monovalent or divalent as indicated by the position of the group in the structural formula. Straight-chain groups are generally preferred. The term "α-hydroxyalkyl" as it is used herein refers to groups derived from α-hydroxy fatty acids, the α-position denoting the carbon adjacent to the carboxyl group of the fatty acid. By "fatty acid residue" is meant the portion of a fatty acid remaining after removal of the —COOH group.

Preferred groups for $R^1$ are $C_{10}$–$C_{36}$ alkyl and α-hydroxy-$C_{10}$–$C_{36}$ alkyl, or either of the two subgroups $C_{14}$–$C_{20}$ alkyl and α-hydroxy-$C_{14}$–$C_{20}$ alkyl or $C_{20}$–$C_{36}$ alkyl and α-hydroxy-$C_{20}$–$C_{36}$ alkyl. Particularly preferred are $C_{20}$–$C_{36}$ alkyl, and the most preferred are saturated $C_{20}$–$C_{36}$ alkyl.

The preferred group for $R^2$ is

Preferred groups for $R^3$ are $C_{12}$–$C_{16}$ saturated straight-chain alkyl, particularly $C_{13}$–$C_{15}$ saturated straight-chain alkyl, with $C_{13}$ and $C_{15}$ saturated straight-chain alkyl as the most preferred.

Many ceramides are naturally occurring in certain plant tissues such as yeast, and also in the mammalian stratum corneum and in other mammalian tissues such as brain tissue and nervous tissue. Ceramides can be extracted from these tissues by methods known in the art. Bovine brain tissue and human spleen tissue are common commercial sources. A mixture termed "ceramides type III" is prepared by the action of phospholipase C on bovine brain sphingomyelin, and the $R^3$ moiety is primarily stearic (saturated 18-carbon) and nervonic (unsaturated 24-carbon) acids. A mixture termed "ceramides type IV" is similar to ceramides type III except that it contains α-hydroxy acids rather than stearic and nervonic acids. Both mixtures are commercially available from chemicals suppliers such as Sigma Chemical Company, St. Louis Mo., USA, and those which are not direct extracts are capable of being prepared by techniques described in the literature, such as Morrison, W. R., *Biochem. Biophys. Acta* 176:537 (1979), and Carter, H. E., et al., *J. Lipid Res.* 2:228 (1961). In general, seven types of ceramides are known, and all are believed to be useful in the practice of this invention.

The components designated herein as "free fatty acids" include α-hydroxy fatty acids and ω-hydroxy fatty acids, and non-hydroxylated fatty acids, both saturated and unsaturated, and both straight-chain and branched-chain. Straight-chain, α-hydroxy and non-hydroxylated fatty acids are preferred. The fatty acids are generally up to 36 carbon atoms in length. Preferred lengths are 12 to 20 carbon atoms.

The essential free fatty acids are linoleic acid (18 carbon atoms, two double bonds) and linolenic acid (18 carbon atoms, three double bonds), including the various isomers of these acids. Nonessential free fatty acids are all other fatty acids, notably those of 12 to 20 carbon atoms. Preferred nonessential free fatty acids are those of 16 to 18 carbon atoms, and the most preferred are stearic and palmitic acids. The free fatty acids may also be supplied in the form of their glycolipid precursors such as triglycerides.

The enzyme β-glucocerebrosidase (β-D-glucosyl-N-acylsphingosine glucohydrolase, E.C. 3.2.1.45) is a lysosomal glycoprotein enzyme that catalyzes the hydrolysis of glucocerebrosides to glucose and ceramides. This enzyme is a naturally occurring human enzyme that is available from commercial suppliers. Certain analogues of the enzyme with similar activity are also commercially available and can likewise be used in this invention. One such analogue is CEREZYME®, which is produced by recombinant DNA technology using mammalian cell culture. This analogue, which is also known is imiglucerase, is a momeric glycoprotein of 497 amino acids, differing from placental glucocerebrosidase by the substitution of histidine for arginine at position 495, and by the modification of the oligosaccharide chains at the glycosylation sites such that they terminate in mannose sugars. Another analogue is CEREDASE® (alglucerase), produced by modification of the oligosaccharide chains of human β-glucocerebrosidase to alter the sugar residues at the non-reducing ends so that they are predominantly terminated with mannose residues. Each of these analogues is available from Genzyme Corporation, Cambridge, Mass., USA.

Phospholipase $A_2$ is a class of enzymes that specifically catalyzes the hydrolysis of the sn-2 acyl or alkyl ester of phosphoglycerides, producing equimolar quantities of lysophospholipids and free fatty acids. Preferred phospholipase $A_2$ (PLA$_2$) enzymes for use in this invention are mammalian secretory PLA$_2$ enzymes and particularly pancreatic Type 1 or Type 5 secretory PLA$_2$ enzymes. Porcine, bovine and human pancreatic PLA$_2$ are commercially available from chemical suppliers, such as Sigma Chemical Company, St. Louis, Mo., USA.

The enzymes β-glucocerebrosidase (or its analogs) and secretory phospholipase $A_2$ can also be applied individually rather than in combination. Application of either one individually will provide partial relief of xeric stress.

In each of the formulations of this invention, the relative amounts of the components may vary and specific proportions are not critical to the invention. In each case, however, certain ranges of proportions are preferred. For the formulations described herein as containing a combination of (a) ceramide, (b) essential free fatty acid, and (c) nonessential free fatty acid, the preferred mole ratios of (a):(b):(c) are about (1–5):(1–5):(1–5). A more preferred mole ratio range is about (1–3):(1–3):(1–3). Alternatively, preferred ratios are those that combine with the cholesterol already present in the lips stratum corneum to achieve a final lipid composition in which the mole ratio of (cholesterol):(ceramide): (essential free fatty acid):(nonessential free fatty acid) is from about 1:1:1:1 to about 3:1:1:1.

The compositions of this invention are applied directly to the lips, and may be incorporated in a cosmetic preparation such as lipstick or a therapeutic or preventive preparation such as lip balm. The preparation may take various forms such as a stick, salve, cream or ointment. The preparations will generally include a vehicle, and any non-toxic and pharmaceutically acceptable vehicle, including those that are known for use in application to lips may be used. Examples are petrolatum, mineral oil, modified or unmodified vegetable oils, silicon-based oils and other synthetic oils, and waxes. Additional ingredients such as pigments, perfumes, sunscreens, and preservatives may also be included.

The following examples are offered for purposes of illustration only.

EXAMPLE 1

This example reports test results that compare the expression of hydrolytic enzymes in human epidermis with the expression of the same enzymes in human lip tissue (oral epithelium). The expression levels were determined by measuring mRNA levels, using both Northern blotting and in situ hybridization. The expression levels were also determined by measuring protein/activity levels by means of at least two of the following methods: immunohistochemistry, in vitro enzyme assay, Western immunoblotting, and in situ zymography. Each of these methods and the manner of applying or adapting them to this type of determination are known in the art.

The results are listed in Table I. In this table, "N.D." signifies that the result was too low to be detectable, and the expression levels are expressed on a relative basis, with the "+" sign denoting the lowest observed levels, and the "++++" denoting the highest observed levels.

TABLE I

Comparison of Enzyme Expression:
Epidermis vs. Oral Epithelium

| | EXPRESSION LEVEL | | | |
|---|---|---|---|---|
| | mRNA | | Protein/Activity | |
| ENZYME | Oral Epithelium | Epidermis | Oral Epithelium | Epidermis |
| β-Glucocerebrosidase | N.D. | ++++ | 0/+ | ++++ |
| Secretory Phospholipase $A_2$ | + | N.D. | + | ++++ |
| Acidic Sphingomyelinase | + | ++++ | + | ++++ |

Table I demonstrates that the expression of these three enzymes is significantly lower in oral epithelium than in epidermal tissues, in accordance with both indicators (mRNA and protein/activity).

EXAMPLE 2

This example reports test results that compare the levels of stratum corneum lipids in human epidermis with those in human lip tissue (oral epithelium). Stratum corneum sheets for testing were obtained by trypsinization, and total lipids were extracted by the Bligh-Dyer method, a method well known in the art (Bligh, E. G., and W. J. Dyer, *Can. J. Biochem. Physiol.* 37: 911–917 (1959). The separation and quantitation of individual lipid fractions were achieved by high-performance thin-layer chromatography.

The results are shown in Table II.

TABLE II

Comparison of Levels of Stratum Corneum Lipids: Epidermis vs. Oral Epithelium

| TISSUE | LIPID WEIGHT PERCENT | | | | | |
|---|---|---|---|---|---|---|
| | Phospho-lipids | Glyco-lipids | Ceramides | Chol-esterol | Free Fatty Acids | Other |
| Epidermis (n = 8) | trace | trace | 50 | 25 | 20 | <5 |
| Lip (n = 3) | 25 | 40 | <5 | 20 | <5 | <5 |

Table II demonstrates that the levels of ceramides and free fatty acids are significantly lower in oral epithelium than in epidermal tissues, while the levels of phospholipids and glycolipids are significantly higher, and the levels of cholesterol are largely unchanged.

EXAMPLE 3

This example illustrates the efficacy of various formulations within the scope of this invention in restoring the lipid barrier function in the lower lips of human subjects. The trans-epithelial water loss (TEWL) was measured by means of an electrolytic water analyzer (MEECO, INC., Warrington, Pa., USA).

The baseline (pretreatment) levels of TEWL were $2.0 \pm 0.025$ mg/cm$^2$/h, as compared to normal epidermal skin which is less than 0.15 mg/cm$^2$/h. The formulations used were as follows:

No. 1: Mixture of bovine ceramide, palmitic acid, and linoleic acid, at a mole ratio of 1:2:2, as a 1.5% (by weight) solution in a propylene glycol and ethanol mixture (7:3 by volume).

No. 2: Mixture of β-glucocerebrosidase and pancreatic secretory lipase, at a concentration of 0.25% in 0.1 M sodium phosphate-buffered saline, pH 5.5.

No. 3: Mixture of bovine ceramide, cholesterol, palmitic acid, and linoleic acid, at a mole ratio of 1:1:2:2, as a 1.5% (by weight) solution in a propylene glycol and ethanol mixture (7:3 by volume).

Vehicle alone: Mixture of propylene glycol and ethanol (7:3 by volume).

The tests were performed on four young adult subjects, ages 25–40, by applying a total of 0.2 mL of each formulation to sites measuring 0.5 cm in diameter on the lower lip. Measurements were taken at 2, 4, and 6 hours after treatment was initiated. The results are shown in Table III, where each entry represents the percentage normalization (i.e., degree of return to the normal value) in TEWL from the baseline level (the higher the percentage, the more effective the treatment) and is the average of three measurements.

TABLE III

Barrier Restoration Test Results on Human Lower Lip

| | Percent Normalization in TEWL | | |
|---|---|---|---|
| Time → | 2 hours | 4 hours | 8 hours |
| Formulation No. 1 | 46 | 62 | 54 |
| Formulation No. 2 | 32 | 64 | 86 |
| Formulation No. 3 | 12 | 16 | 4 |
| Vehicle alone | −6 | −2 | 0 |

Table III demonstrates that each of the formulations lowered the TEWL relative to the vehicle alone and therefore had a positive effect on barrier restoration. Formulations 1 and 2 however were significantly superior to Formula 3.

The foregoing descriptions are offered primarily for purposes of illustration. It will be readily apparent to those skilled in the art that the components, proportions, additional ingredients, methods of administration, and other parameters of the invention described herein can be modified or substituted in various ways while still remaining within the spirit and scope of the invention.

What is claimed is:

1. A method for treating lips of a human subject for prevention or repair of xeric stress, said method comprising applying to said lips a barrier function maintaining amount of a composition comprising the following components as the only lipids in the composition:

(a) one or more ceramides, (b) one or more essential free fatty acids, and (c) one or more nonessential free fatty acids of 12 to 20 carbon atoms each, at (a):(b):(c) mole ratios of about (1–5):(1–5):(1–5).

2. A method in accordance with claim 1 in which said one or more essential free fatty acids are members selected from the group consisting of linoleic and linolenic acids.

3. A method in accordance with claim 1 in which said component (b) is linoleic acid.

4. A method in accordance with claim 1 in which said one or more nonessential free fatty acids are those having 16 to 18 carbon atoms each.

5. A method in accordance with claim 1 in which said one or more nonessential free fatty acids are members selected from the group consisting of palmitic and stearic acids.

6. A method in accordance with claim 1 in which component (c) is palmitic acid.

7. A method in accordance with claim 1 in which said one or more ceramides are members selected from the group consisting of bovine ceramides, types III and IV.

8. A method in accordance with claim 1 in which said mole ratios are about (1–3):(1–3):(1–3).

9. A method in accordance with claim 1 in which component (a) is a bovine ceramide, component (b) is linoleic acid, and component (c) is palmitic acid.

* * * * *